United States Patent [19]
Momin et al.

[11] Patent Number: 6,146,632
[45] Date of Patent: Nov. 14, 2000

[54] VACCINES

[75] Inventors: Patricia Marie Momin, Brussels; Nathalie Marie-Josephe Garcon, Wavre, both of Belgium

[73] Assignee: SmithKline Beecham Biologicals s.a., Rixensart, Belgium

[21] Appl. No.: 08/663,289

[22] PCT Filed: Dec. 20, 1994

[86] PCT No.: PCT/EP94/04246

§ 371 Date: Jul. 2, 1996

§ 102(e) Date: Jul. 2, 1996

[87] PCT Pub. No.: WO95/17210

PCT Pub. Date: Jun. 29, 1995

[30] Foreign Application Priority Data

Dec. 23, 1993 [GB] United Kingdom .................. 9326253

[51] Int. Cl.[7] .................. A61K 39/00; A61K 39/385; A61K 39/12; A61K 39/21
[52] U.S. Cl. .................. 424/184.1; 424/193.1; 424/204.1; 424/207.1; 424/208.1; 424/209.1; 424/211.1; 424/225.1; 424/226.1; 424/227.1; 424/228.1; 424/229.1; 424/230.1; 424/231.1; 424/234.1; 424/249.1; 424/253.1; 424/258.1; 424/263.1; 424/268.1; 424/273.1
[58] Field of Search .................. 424/278.1, 184.1, 424/193.1, 204.1, 207.1, 208.1, 209.1, 211.1, 225.1, 226.1, 227.1, 228.1, 229.1, 230.1, 231.1, 234.1, 249.1, 253.1, 258.1, 263.1, 268.1, 273.1

[56] References Cited

U.S. PATENT DOCUMENTS 4,912,094  3/1990  Myers et al. .
5,057,540  10/1991  Kensil et al. .
5,554,372  9/1996  Hunter .
5,709,879  1/1998  Barchfeld .
5,723,130  3/1998  Hancock et al. .

FOREIGN PATENT DOCUMENTS 0 382 271  8/1990  European Pat. Off. .
0 399 843  11/1990  European Pat. Off. .
WO 88/09336  12/1988  WIPO .
WO 92/16556  10/1992  WIPO .
WO 94/00153  1/1994  WIPO .
WO94/27636  12/1994  WIPO .
WO 95/17209  6/1995  WIPO .

OTHER PUBLICATIONS

Haynes (Science vol. 260 May 28, 1993 pp 1279–1286).

Johnston et al (Science vol. 260 May 28, 1993 pp 1286–1293).

Mester et al (Review of Infectious Diseases vol. 13 1991 pp 5935–945).

McElratl et al (PNAS USA, vol. 93 Apr. 1996 pp 3972–3977).

*Primary Examiner*—Albert Navarro
*Attorney, Agent, or Firm*—Zoltan Kerekes; Stephen Venetianer; Charles M. Kinzig

[57] ABSTRACT

The present invention provides vaccine compositions comprising an oil-in-water emulsion optionally with 3 De-O-acylated monophosphoryl lipid A and QS21. The vaccines compositions are potent inducers of a range of immune responses.

15 Claims, 7 Drawing Sheets

ANTIGEN HbsAg

| GROUP | FORMULATION | IgG1 | | | IgG2a | | | IgG2b | | |
|---|---|---|---|---|---|---|---|---|---|---|
| | | PostII5 | PostII7 | PostII15 | PostII5 | PostII 7 | PostII15 | PostII5 | PostII7 | PostII15 |
| 1 | SB62 | 275 | 3861 | 4171 | 44 | 479 | 1134 | 81 | 700 | 704 |
| 2 | QS21 MPL | 33 | 2533 | 2146 | 176 | 5301 | 5464 | 138 | 2235 | 1160 |
| 3 | QS21 MPL SB62 | 130 | 1248 | 1774 | 498 | 8551 | 15806 | 371 | 5107 | 3606 |
| 4 | AL(OH)3 MPL | 187 | 1138 | 2501 | 129 | 1832 | 4059 | 249 | 2621 | 1441 |
| 5 | AL(OH)3 | 130 | 936 | 1562 | 13 | 128 | 658 | 265 | 192 | 951 |
| 6 | plain | 6 | 426 | 490 | 6 | 90 | 87 | 5 | 226 | 183 |
| 7 | neg Controls | 5 | 5 | 5 | 5 | 5 | 5 | 5 | 5 | 5 |

FIG. 2A

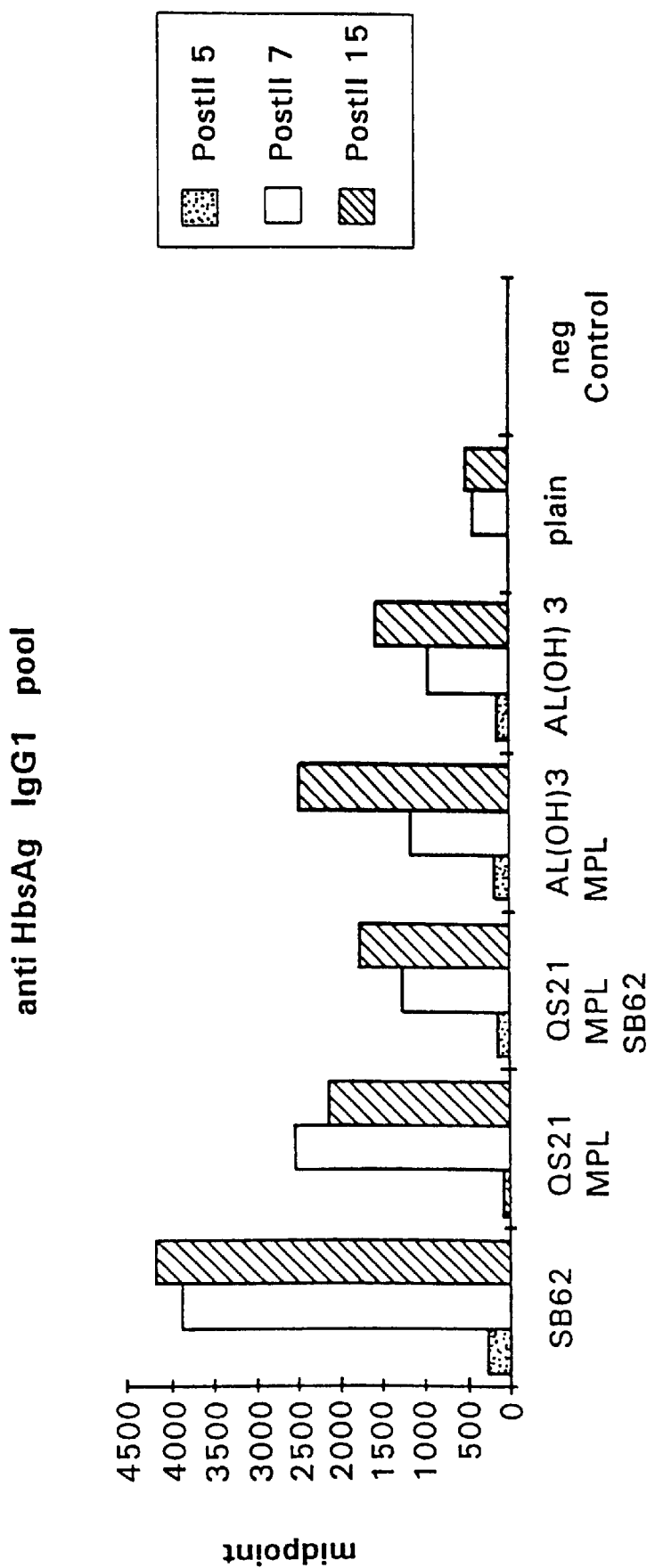

Anti-OspA Abs titers (Igt) after immunization of Balb/C mice with different formulations of Lipoprotein OspA Anti-OspA Abs titers (IgG2a) after immunization of Balb/C mice with different formulations of Lipoprotein OspA

VACCINES

The present invention relates to novel vaccine formulations, to methods of their production and to their use in medicine. In particular, the present invention relates to an oil in water emulsion. Such emulsions comprise tocopherol, squalene, TWEEN 80 (polyoxyethelene sorbitan monooleate) Span 85 and Lecithin and have useful adjuvant properties. Vaccines containing QS21, an Hplc purified non-toxic fraction derived from the bark of Quillaja Saponaria Molina, and/or 3 De-O-acylated monophosphoryl lipid A (3 D-MPL), together with such oil in water emulsions also form part of the invention.

3 De-O-acylated monophosphoryl lipid A is known from GB2220 211 (Ribi). Chemically it is a mixture of 3 De-O-acylated monophosphoryl lipid A with 4, 5 or 6 acylated chains and is manufactured by Ribi Immunochem Montana. A preferred form of 3 De-O-acylated monophosphoryl lipid A is disclosed in International Patent Application No. 92/116556.

QS21 is a Hplc purified non toxic fraction of a saponin from the bark of the South American tree Quillaja Saponaria Molina and its method of its production is disclosed (as QA21) in U.S. Pat. No. 5,057,540.

Oil in water emulsions per se are known in the art, and have been suggested to be useful as adjuvant compositions (EPO 399843).

The present invention is based on the surprising discovery that an oil in water emulsion of the present invention, which unlike emulsions of the prior art contain tocopherol, as such or in combination with QS21 and/or 3 D-MPL enhance immune responses to a given antigen. Such enhancement available affords better immunological responses than hitherto before.

Additionally the oil in water emulsions of the present invention when formulated with 3 D-MPL and QS21 are preferential stimulators of IgG2a production and TH1 cell response. This is advantageous, because of the known implication of $TH_1$ response in cell mediated response. Indeed in mice induction of IgG2a is correlated with such an immune response.

For example a vaccine formulation of the HIV antigen gp 120 in such a combination results in a powerful synergistic induction of gp 120 protein specific immune responses.

The observation that it is possible to induce strong cytolytic T lymphocyte responses significant as these responses, in certain animal models have been shown to induce protection against disease.

The present inventors have shown that the combination of the adjuvants QS21 and 3D-MPL together with an oil in water emulsion with an antigen results in a powerful induction of CS protein specific CTL in the spleen. QS21 also enhances induction of CTL on its own, while 3D-MPL does not.

Induction of CTL is easily seen when the target antigen is synthesised intracellularly (e.g. in infections by viruses, intracellular bacteria, or in tumours), because peptides generated by proteolytic breakdown of the antigen can enter the appropriate processing pathway, leading to presentation in association with class I molecules on the cell membrane. However, in general, pre-formed soluble antigen does not reach this processing and presentation pathway, and does not elicit class I restricted CTL. Therefore conventional non-living vaccines, while eliciting antibody and T helper responses, do not generally induce CTL mediated Immunity. The combination of the two adjuvants QS21 and 3D-MPL together with an oil in water emulsion can overcome this serious limitation of vaccines based or recombinant proteins, and induce a wider spectrum of immune responses.

CTL specific for CS protein have been shown to protect from malaria in mouse model systems (Romero et al. Nature 341:323 (1989)). In human trials where volunteers were immunised using irradiated sporozoites of *P. falciparum*, and shown to be protected against subsequent malaria challenge, induction of CTL specific for CS epitopes was demonstrated (Malik et al. Proc. Natl. Acad. Sci. U.S.A. 88:3300 (1991)).

The ability to induce CTL specific for an antigen administered as a recombinant molecules is relevant to malaria vaccine development, since the use of irradiated sporozoites would be impractical, on the grounds of production and the nature of the immune response.

RTS is a hybrid protein comprising substantially all the C-terminal portion of the circumsporozoite (CS) protein of *P. falciparum* linked via four amino acids of the $preS_2$ portion of Hepatitis B surface antigen to the surface (S) antigen of hepatitis B virus. It's full structure is disclosed in co-pending International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S.

In addition to human immunodeficiency virus and malaria vaccines, the ability to induce CTL responses would benefit vaccines against herpes simplex virus, cytomegalovirus, and generally all cases where the pathogen has an intracellular life stage.

Likewise, CTL specific for known tumour antigens could be induced by a combination of a recombinant tumour antigen and the two adjuvants. This would allow the development of anti cancer vaccines.

In certain systems, the combination of 3D-MPL and QS21 together with an oil in water emulsion have been able to synergistically enhance interferon γ production. The present inventors have demonstrated the potential of 3D-MPL and QS21 together with an oil in water emulsion by utilising a herpes simplex antigen known as $gD_2t$. $gD_2t$ is a soluble truncated glycoprotein D from HSV-2 and is produced in CHO cells according to the methodology Berman et al. Science 222 524–527.

IFN-γ secretion is associated with protective responses against intracellular pathogens, including parasites, bacteria and viruses. Activation of macrophages by IFN-γ enhances intracellular killing of microbes and increases expression of Fc receptors. Direct cytotoxicity may also occur, especially in synergism with lymphotoxin (another product of TH1 cells). IFN-γ is also both an inducer and a product of NK cells, which are major innate effectors of protection. TH1 type responses, either through IFN-γ or other mechanisms, provide preferential help for IgG2a imnmunoglobulin isotypes.

Glycoprotein D is located on the viral envelope, and is also found in the cytoplasm of infected cells (Eisenberg R. J. et al. J. of Virol. 1980±428–435). It comprises 393 amino acids including a signal peptide and has a molecular weight of approximately 60 kD. Of all the HSV envelope glycoproteins this is probably the best characterized (Cohen et al. J. Virology 60 157–166). In vivo it is known to play a central role in viral attachment to cell membranes. Moreover, glycoprotein D has been shown to be able to elicit neutralizing antibodies in vivo (Eing et al. J. Med Virology 127: 59–65). However, latent HSV2 virus can still be reactivated and induce recurrence of the disease despite the presence of high neutralizing antibodies titre in the patients sera. It is therefore apparent that the ability to induce neutralizing antibody alone is insufficient to adequately control the disease.

In order to prevent recurrence of the disease, any vaccine will need to stimulate not only neutralizing antibody, but also cellular immunity mediated through T-cells, particularly cytotoxic T-cells.

In this instance the $gD_2t$ is HSV2 glycoprotein D of 308 amino acids which comprises amino acids 1 though 306 of the naturally occurring glycoprotein with the addition of Asparagine and Glutamine at the C terminal end of the truncated protein. This form of the protein includes the signal peptide which is cleaved to yield a mature 283 amino acid protein. The production of such a protein in Chinese Hamster ovary cells has been described in Genentech's European patent EP-B-139 417.

The mature truncated glycoprotein D (rgD2t) or equivalent proteins secreted from mammalian cells, is preferably used in the vaccine formulations of the present invention.

The formulations of the present invention are very effective in inducing protective immunity in a genital herpes model in guinea pigs. Even with very low doses of antigen (e.g. as low as 5 µg rgD2t) the formulations protect guinea pigs against primary infection and also stimulate specific neutralising antibody responses. The inventors, utilising formulation of the present invention, have also demonstrated Effector cell mediated responses of the TH1 type in mice.

Accordingly, in one preferred embodiment of the present invention provides a vaccine or pharmaceutical formulation comprising an antigen in conjunction with 3 De-O-acylated monophosphoryl lipid A, QS21 and an oil in water emulsion wherein the oil in water emulsion comprises a metabolisible oil, such as squalene, alpha tocopherol and TWEEN 80 (polyoxyethelene sorbitan monooleate). Such a formulation is suitable for a broad range of monovalent or polyvalent vaccines. Additionally the oil in water emulsion may contain span 85. A preferred form of 3 De-O-acylated monophosphoryl lipid A is disclosed in International patent application published under No. 92116556—SmithKline Beecham Biologicals s.a.

The oil in water emulsion may be utilised on its own or with other adjuvants or immuno-stimulants and therefore an important embodiment of the invention is an oil in water formulation comprising squalene or another metabolisable oil, alpha tocopherol, and TWEEN 80 (polyoxyethelene sorbitan monooleate). The oil in water emulsion may also contain span 85 and/or Lecithin.

Preferably the vaccine formulations will contain an antigen or antigenic composition capable of eliciting an immune response against a human or animal pathogen, which antigen or antigenic composition is derived from HIV-1, (such as gp120 or gp160), any of Feline Immunodeficiency virus, human or animal herpes viruses, such as gD or derivatives thereof or Immediate Early protein such as ICP27 from HSV1 or HSV2, cytomegalovirus ((esp Human)(such as gB or derivatives thereof), Varicella Zoster Virus (such as gpI, II or III), or from a hepatitis virus such as hepatitis B virus for example Hepatitis B Surface antigen or a derivative thereof, hepatitis A virus, hepatitis C virus and hepatitis E virus, or from other viral pathogens, such as Respiratory Syncytial virus, human papilloma virus or Influenza virus, or derived from bacterial pathogens such as Salmonella, Neisseria, Borrelia (for example OspA or OspB or derivatives thereof), or Chlamydia, or Bordetella for example P.69, PT and FHA, or derived from parasites such as plasmodium or Toxoplasma.

The formulations may also contain an anti-tumour antigen and be useful for immunotherapeutically treating cancers.

In an immunotherapeutic animal model for B cell lymphoma, where BCL-1 mouse lymphoma cells are administered intaperitonelly to Balb/c mice on day 0, and mice are vaccinated on days 3, 10 and 20 with the BCL-1 Idlotype, formulation SB62/MPL/QS21 stands out as the most potent, both with respect to antibody titers, and with respect to survival (the only group with 100% survival). Similarly the ability of this formulation to stimulate cytotoxic T lymphocytes to the antigens included make them a good candidate for formulation of cancer antigens (e.g. melanoma antigens MAGE-1 and MAGE-3 for immunotherapy of tumors by active vaccination).

The formulation may also be useful for utilising with herpetic light particles such as described in International Patent Application No. PCT/GB92/00824 and, International Patent Application No. PCT/GB92/00179.

Derivatives of Hepatitis B Surface antigen are well known in the art and include, inter alia, those $PreS_1$, $PreS_2$ S antigens set forth described in European Patent applications EP-A-414 374; EP-A-0304 578, and EP 198-474. In one preferred aspect the vaccine formulation of the invention comprises the HIV-1 antigen, gp 120, especially when expressed in CHO cells. In a further embodiment, the vaccine formulation of the invention comprises $gD_2t$ as hereinabove defined.

In a further aspect of the present invention there is provided a vaccine as herein described for use in medicine.

The ratio of QS21:3D-MPL will typically be in the order of 1:10 to 10:1; preferably 1:5 to 5:1 and often substantially 1:1. The preferred range for optimal synergy is 2.5:1 to 1:1 3D MPL:QS21. Typically for human administration QS21 and 3D MPL will be present in a vaccine in the range 1 µg–100 µg, preferably 10 µg–50 µg per dose. Typically the oil in water will comprise from 2 to 10% squalene, from 2 to 10% alpha tocopherol and from 0.3 to 3% TWEEN 80 (polyoxyethelene sorbitan monooleate). Preferably the ratio of squalene:alpha tocopherol is equal or less than 1 as this provides a more stable emulsion. Span 85 may also be present at a level of 1%. In some cases it may be advantageous that the vaccines of the present invention will further contain a stabiliser.

Vaccine preparation is generally described in New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 µg of protein, preferably 2–100 µg, most preferably 4–40 µg. An optimal amount for a particular vaccine can be ascertained by standard studies involving observation of appropriate immune responses in subjects. Following an initial vaccination, subjects may receive one or several booster immunisation adequately spaced.

The formulations of the present invention maybe used for both prophylatic and therapeutic purposes.

Accordingly in one aspect, the invention provides a method of treatment comprising administering an effective amount of a vaccine of the present invention to a patient.

The following examples illustrate the invention.

DESCRIPTION OF DRAWINGS

FIGS. 2A–2D, Graphs showing the anti Hepatitis B IgG1, IgG2a and IgG2b titres at three time points (after priming and after each of two booster vaccinations) induced by a vaccine consisting of RTS,S antigen adjuvanted with the oil in water emulsion SB26, in combination with 3D-MPL and QS21.

EXAMPLES

Example 1

Figure 1:
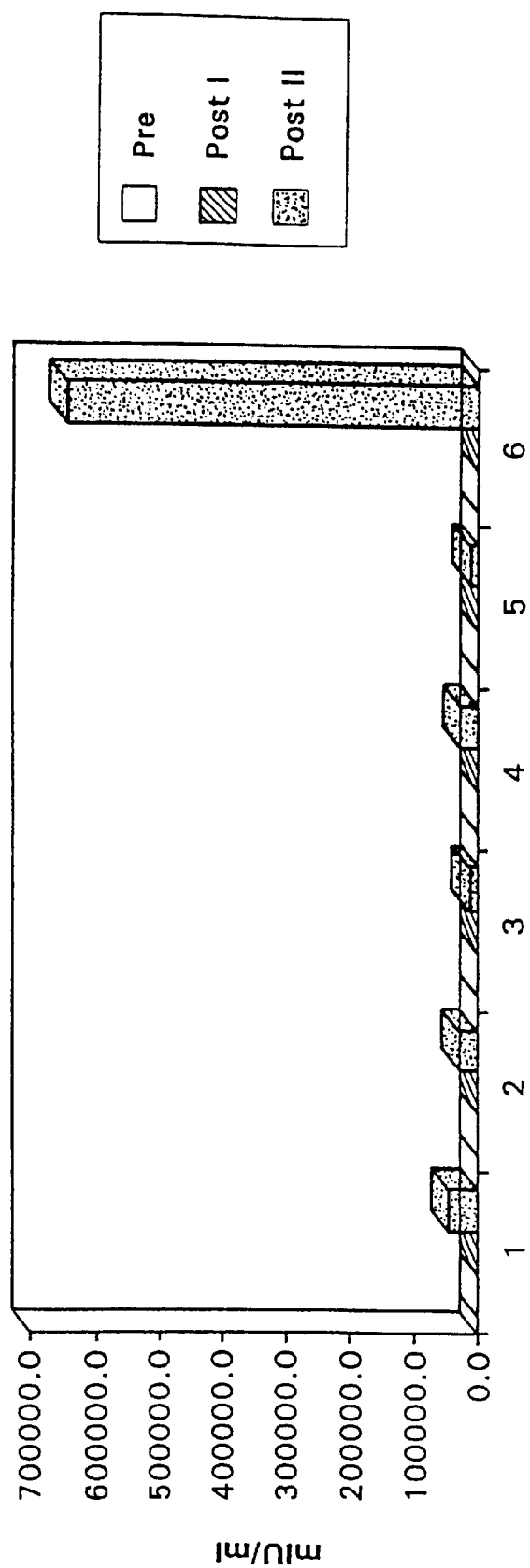
FIG. 1, Graph showing the anti Hepatitis B total immunoglobulin titres at three time points (after priming and after each of two booster vaccinations) induced by a vaccine consisting of RTS,S antigen adjuvanted with the oil in water emulsion SB60, in combination with 3D-MPL and QS21.

Vaccine Formulation Comprising the gp 120 Antigen of HIV-1

The two adjuvant formulations were made each comprising the following oil in water emulsion component.

SB26: 5% squalene 5% tocopherol 0.4% TWEEN 80 (polyoxethelene sorbitan monooleate); the particle size was 500 nm size SB62: 5% Squalene 5% tocopherol 2.0% TWEEN 80 (polyoxethelene sorbitan monooleate); the particle size was 180 nm 1(a) Preparation of Emulsion SB62 (2 Fold Concentrate)

TWEEN 80 (polyoxethelene sorbitan monooleate) is dissolved in phosphate buffered saline (PBS) to give a 2% solution in the PBS. To provide 100 ml two fold concentrate emulsion 5 g of DL alpha tocopherol and 5 ml of squalene are vortexed to mix thoroughly. 90 ml of PBS/Tween solution is added and mixed thoroughly. The resulting emulsion is then passed through a syringe and finally microfluidised by using an M110S microfluidics machine. The resulting oil droplets have a size of approximately 180 nm.

1(b) Preparation of Emulsion SB26

This emulsion was prepared in an analogous manner utilising 0.4% TWEEN 80 (polyoxethelene sorbitan monooleate).

1(c) Other Emulsions as Depicted in Table 1 Were Made in an Analogous Manner

These are tested in the experiments as detailed in the following examples.

1(d) Preparation of gp 120 QS21/3D MPL Oil in Water Formulation

To the emulsion of 1 a) or b) or c) an equal volume of twice concentrated rgp 120 (either 20 μg or 100 μg) was added and mixed. This was combined with 50 μg/ml of 3D-MPL and 20 μg/ml of QS21 to give the final formulation. Buffer was sed according to salt content and pH.

Table 3 shows the effectiveness of SB26, utilising gp 120 from HIV and 50 μg/ml 3D MPL (MPL) and 20 μg/ml of QS21. The results show the geometric mean titre (GMT) after the second (PII) and third (PIII) inoculations as well as cell mediated responses (CMI) to lymphocyte propheration and γ interferon production.

Example 2

Introduction: Evaluation of an HIV gp 120 Emulsion System

In this experiment, four emulsions are compared [SB26, SB62, SB40, SB61]. The influence of each formulation's component (antigen, emulsion, 3D-MPL, QS21) is evaluated.

2(b) Groups of Animals Utilised

There are 22 groups of 5 animals each group received a different vaccine formulation.

gr 1–4: gp 120 (10 μg)/no emuls±[3D-MPL, QS21]
gr 5–9: gp 120 (10 μg)/SB26±[3D-MPL, QS21]
gr 10: no antigen/SB26+[3D-MPL, QS21]
gr 11–12: gp 120 (10 μg)/SB62±[3D-MPL, QS21]
gr 13–16: gp 120 (10 μg)/SB40±[3D-MPL, QS21]
gr 17–20: gp 120 (10 μg)/SB61±[3D-MPL, QS21]
gr 21–22: gp 120 (5 μg)/SB26±[3D-MPL, QS21]

Assays: antibody titers to gp 120W61D and isotype analysis (all groups)

2(c) Immunization and Bleeding Schedule animals were immunized with gp 120W61D, formulated in different o/w emulsions in the presence of 5 μg 3D-MPL and 5 μg QS21 per dose. Negative controls received the equivalent formulations without any antigen.

animals were immunized subcutaneously at day 0 and 14. Each injection dose was administered in a 100 μl volume.

blood samples were obtained before Immunization (day 0) and after Immunization on days 14 (post I), 21 and 28 (7 and 14d. post II).

2(d) Analysis of the Serological Response the 14 days post I and post II serological response was evaluated in a direct ELISA assay to gp 120W61D.

the 14 days post II response was also characterized regarding the isotypes of gp 120W61D specific antibodies induced in mice after immunization.

Results and Discussion

The results are depicted on Table 2.

a) Comparison of Emulsions in the Presence or Absence of 3D-MPL/QS21

Addition of emulsions SB26, SB40 or SB62 to the antigen induces higher antibody titers; In the absence of immunostimulants, the gp 120 specific antibodies are essentially IgG1.

Addition of immunostimulants 3D-MPL and QS21 induces a huge serological response and a shift of antibodies from IgG1 type to IgG2a/IgG2b: This correlated with cell mediated immunity.

The preferred combination is [SB26+MPL+QS21].

c) gp 120/SB26 Formulation

No significant difference in serological response is observed between group 8 and group 9: addition of the gp 120 before or after the other components of the formulation.

d) Antigen Dose

Both 5 and 10 μg of gp 120 formulated in SB26 induce high serological response (groups 5–8 and 21–22).

Example 3

HSV rgD$_2$t Formulation

In analogous manner to that set forth in Example 1a) formulation comprising the herpes simplex antigen rgD$_2$t was made and used to vaccinate guinea pigs. Such formulation induced protection against both recurrent and initial disease in the guinea pig model.

Example 4

Screening of Adjuvants for Induction of Protective Anti Lymphoma Responses Using Idiotype as Immunogen Therapeutic vaccination of Balb/c mice with idiotype from BCL1 lymphoma cells.

A review of the BALB/C B-cell lymphoma model is discussed by Yefenoh et al. Current opinions Immunobiology 1993 5:740–744.

Groups of 10 mice are injected (ip) with $10^4$ tumor cells at day 0, and vaccinated with 100 μg of KLH-coupled immunoglobulin directed against BCL 1 epitoped (ratio of KLH/Ig:1/1), in different adjuvant formulations at days 3, 10, 20 (sc immunization in the back). Level of serum antibodies to KLH and to idiotype, as well as mouse death are monitored.

| group # | Formulations tested: adjuvant | MPL: 10 μg |
|---|---|---|
| 1 | none (no antigen) | QS21: 10 μg |
| 2 | none | |
| 3 | Freund | |
| 4 | Alum | |
| 5 | Alum/MPL | |
| 6 | Alum/MPL/QS21 | |
| 7 | QS21 | |
| 8 | MPL/QS21 | |
| 9 | SB62MPL | |
| 10 | SB62/MPL/QS21 | | groups 12–15: different adjuvants without antigen

Formulations 8, 9, 10, behaved consistenly better as compared to the others.

Formulation 10 stands out as the most potent, both with respect to antibody titers, and with respect to survival (the only group with 100% survival).

Example 5

Various Formulations of RTS,S a) Evaluated in Monkeys

RTS,S is described in International patent application no. WO93/10152 and was formulated for vaccination of Rheusus monkeys. Five animals were in each group:

| Group I | RTS,S, 3D-MPL(50μ), AL(OH)$_3$ |
|---|---|
| Group II | RTS,S, QS21(20μ), AL(OH)$_3$ |
| Group III | RTS,S, 3D-MPL(50μ), QS21(20μ) |
| Group IV | RTS,S, 3D-MPL(50μ), QS21 AL(OH)$_3$ |
| Group V | RTS,S, 3D-MPL(10μ), QS21 AL(OH)$_3$ |
| Group VI | RTS,S, 3D-MPL(50μ), QS21 SB60 |

The animals were inoculated and bled at 14 days post first immunisation and 12 days post second immunisation and tested for Anti hepatitis B surface antigen immunoglobulin. As can be seen from FIG. 1, animals receiving RTS,S, in SB60 had antibody titres almost six fold higher than any other group.

b) Various Formulations of RTS,S—Evaluated in Mice 7 groups of animals received the following formulations

| Group 1 | RTS,S SB62 |
|---|---|
| Group 2 | RTS,S QS21 3D-MPL |
| Group 3 | RTS,S QS21 3D-MPL SB62 |
| Group 4 | RTS,S 3D-MPL A1(OH)$_3$ |
| Group 5 | RTS,S A1(OH)$_3$ |
| Group 6 | Plain |
| Group 7 | Negative control |

(RTS,S –5 μg/dose, 3 D-MPL 5 μg/dose QS21 5 μg/dose)

Figure 2C:
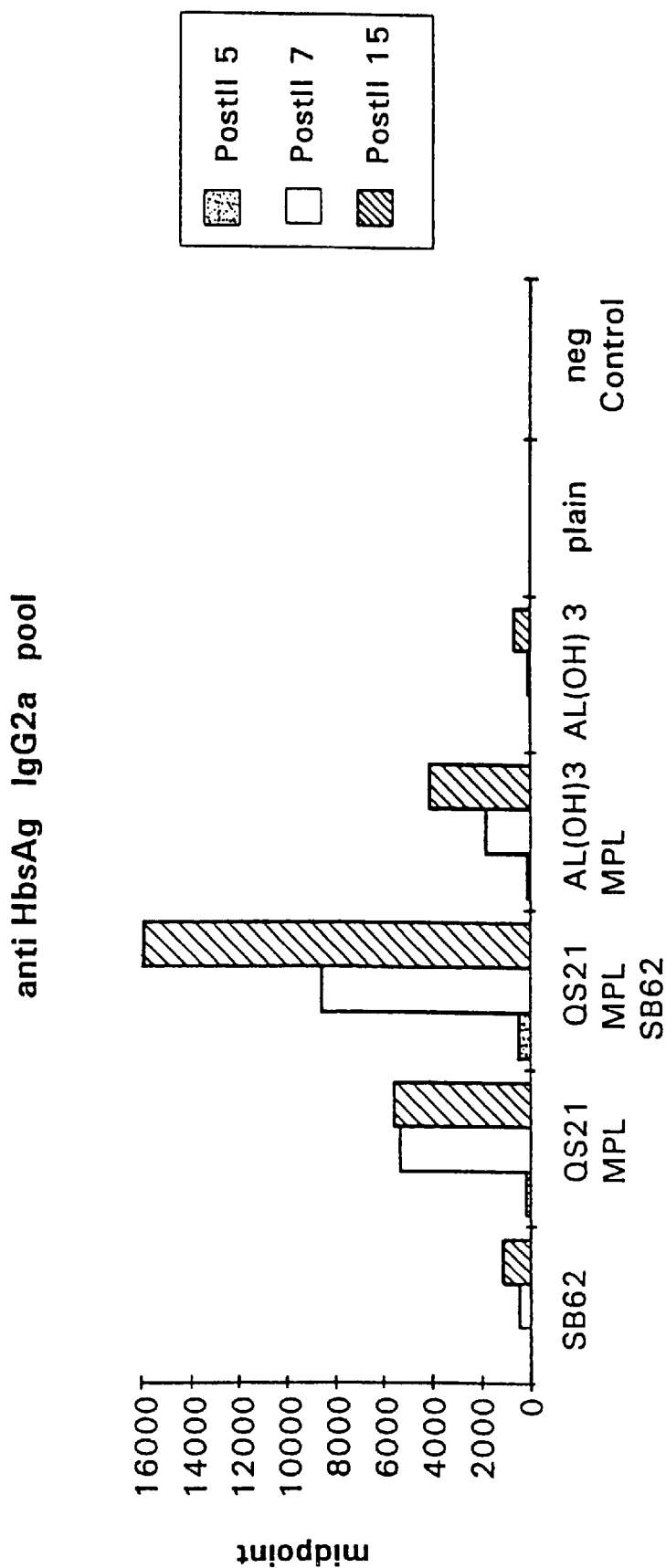
Figure 2D:
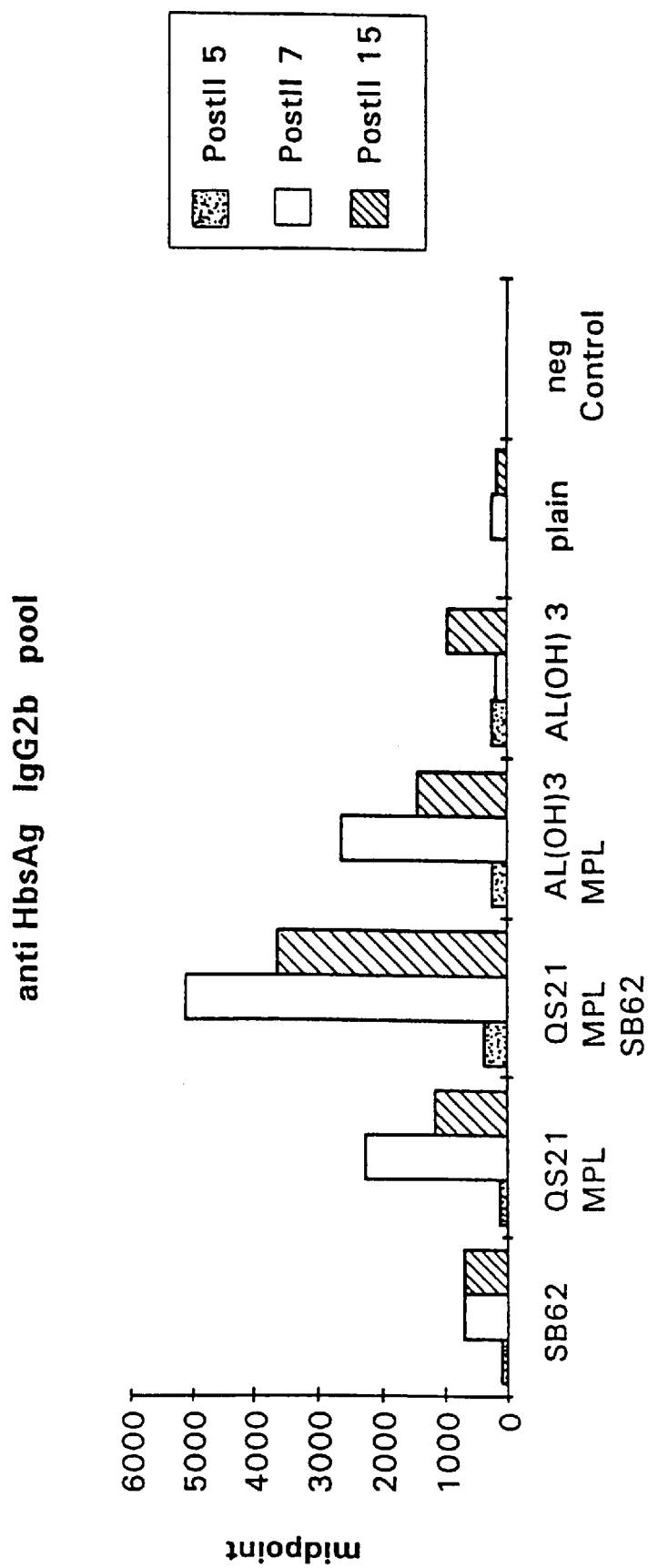

The animals were inoculated and bled at 15 days post first immunisation and at day 7 and 15 post second immunisation and assayed for anti HBSAg antibody subtype. As can be seen from FIG. 2, the emulsion SB62 when formulated with QS21 and 3D-MPL MPL enhances preferentially and in a synergistic fashion the IgG2a antibody response while SB62 alone or 3 D-MPL/QS21 induce a poor I gG2a response.

Example 6

Evaluation of Different B Burgdorferi OspA Formulations 6.1 Evaluation of Different Formulations of B Burgdorferi ZS7 Osp A Lipoproteins OspA lipoprotein for B burgdorferi is described in European Patent Application 0418 827 Max Plank et al.

The following formulations were tested in balb/c mice

1. OspA+A1(OH)$_3$
2. OspA+A1(OH)$_3$+3D-MPL (10μ)
3. OspA+A1(OH)$_3$+3D-MPL (30μ)
4. OspA+A1(OH)$_3$+3D-MPL (10μ)+QS21 (5μ)
5. OspA+A1(OH)$_3$+3D-MPL (30μ)+QS21 (15μ)
6. OspA+SB60+3D-MPL (10μ)+QS21 (5μ)
7. OspA+SB60+3D-MPL (30μ)+QS21 (15μ)

and antibody titres and sub types studied seven days following a first inoculation and seven days post second inoculation (inoculations were at day 0, and 14).

Figure 3A:
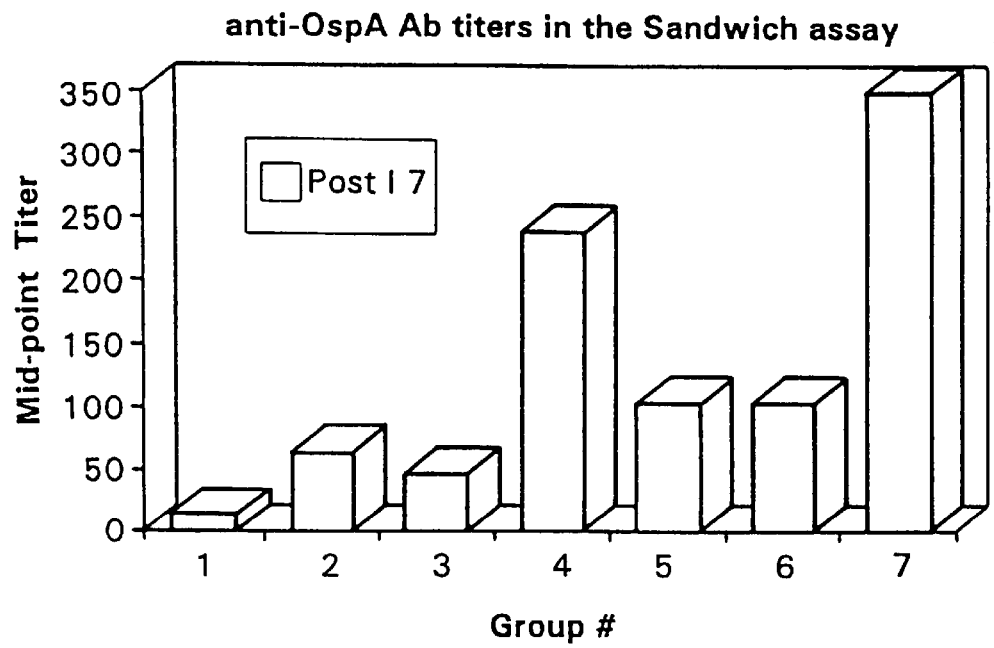
FIGS. 3A–3B, Graphs showing the anti lipoprotein-OspA immunoglobulin titres at two time points (7 days after priming and 7 days after a booster vaccination) induced by vaccines consisting of RTS,S antigen adjuvanted with either the oil in water emulsion SB60, in combination with 3D-MPL and QS21, or adjuvanted with alumium hydroxide.
Figure 3B:
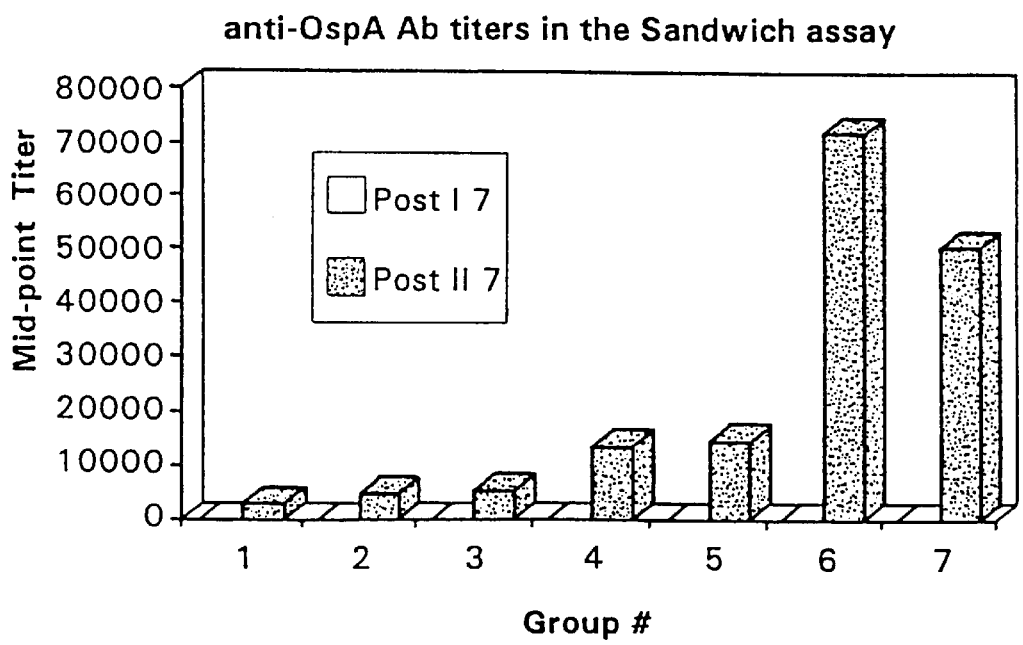
Figure 4A:
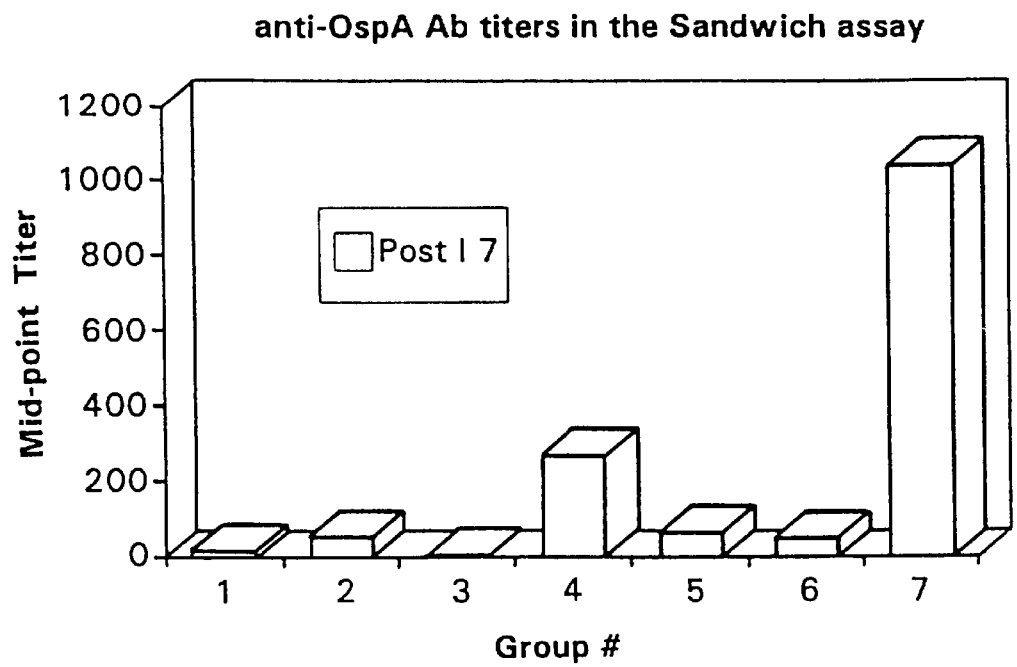
FIGS. 4A–4B, Graphs showing the anti lipoprotein-OspA IgG2a titres at three time points (7 days after priming and 7 days after a booster vaccination) induced by a vaccine consisting of RTS,S antigen adjuvanted with the oil in water emulsion SB60, in combination with 3D-MPL and QS21.
Figure 4B:
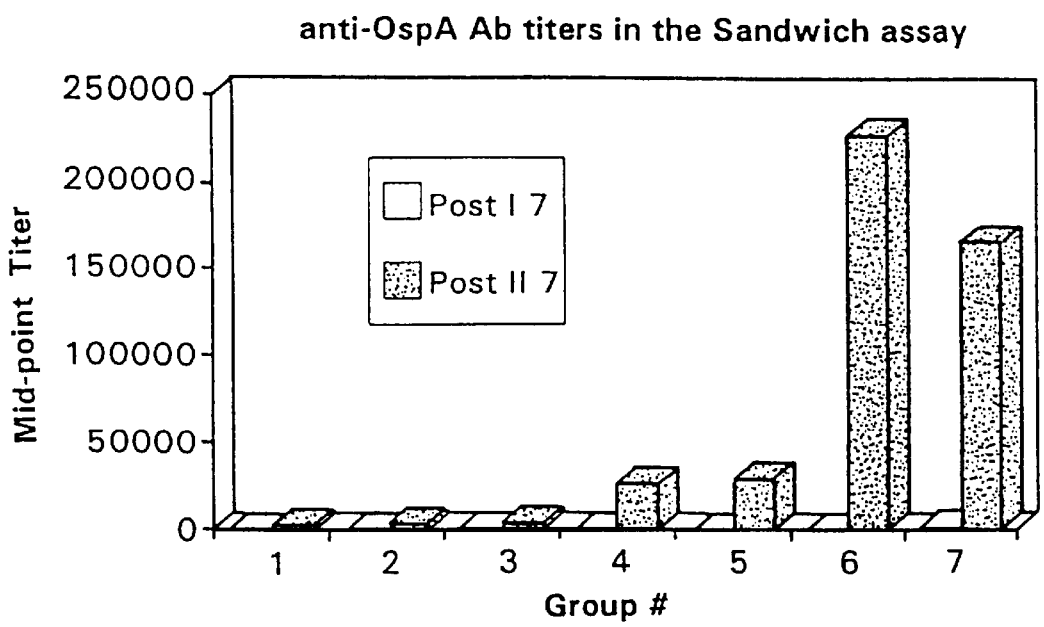

The results depicted graphically in FIGS. 3 and 4 and show that the formulations of the present invention induce high levels of antibodies and these are preferentially of the IgG2a subtype.

Example 7 a) HSV-2 ICP 27

Female Balb/c mice were immunized on day 0 and day 14 in the hind foot-pads with various formulations of NS1-ICP27. Each injection contained 5 μg of NS1-ICP27 and combinations of SB26 oil-in-water emulsion, QS21 (10 μg) and MPL (25 μg).

Popliteal lymphnode cells were obtained on day 28 and stimulated in vitro with syngeneic P815 cells transfected with the ICP27 gene. The cultures were then tested for specific cytolytic activity on P815 target cells transfected with ICP27 and P815 ICP27 negative controls.

Specific lysis results at different effector:target (E:T) ratios for different immunization groups were as follows:

| | ICP 27 (5 µg) | |
|---|---|---|
| E:T | P815 | P815 transfected with ICP 27 clone 121 |
| 100:1 | −1 | 0 |
| 30:1 | −2 | −3 |
| 10:1 | 3 | 0 |
| 3:1 | 1 | 0 |
| 1:1 | 2 | 2 |
| 0.3:1 | 2 | 2 |

| | ICP 27 (5 µg) + MPL (25 µg) | |
|---|---|---|
| E:T | P815 | P815 transfected with ICP 27 clone 121 |
| 100:1 | 5 | 7 |
| 30:1 | 2 | 2 |
| 10:1 | 1 | 2 |
| 3:1 | −1 | −1 |
| 1:1 | −2 | −2 |
| 0.3:1 | −4 | −1 |

| | ICP 27 (5 µg) + QS21 (10 µg) | |
|---|---|---|
| E:T | P815 | P815 transfected with ICP 27 clone 121 |
| 100:1 | 4 | 17 |
| 30:1 | 5 | 10 |
| 10:1 | 3 | 7 |
| 3:1 | 4 | 5 |
| 1:1 | 3 | 5 |
| 0.3:1 | 0 | 1 |

| | ICP 27 (5 µg) + SB26 | |
|---|---|---|
| E:T | P815 | P815 transfected with ICP 27 clone 121 |
| 100:1 | 5 | 20 |
| 30:1 | 1 | 19 |
| 10:1 | 2 | 12 |
| 3:1 | −2 | 7 |
| 1:1 | 1 | 5 |
| 0.3:1 | 1 | 2 |

| | ICP 27 (5 µg) + MPL (25 µg) + QS21 (10 µg) | |
|---|---|---|
| E:T | P815 | P815 transfected with ICP 27 clone 121 |
| 100:1 | 4 | 13 |
| 30:1 | 5 | 12 |
| 10:1 | 4 | 17 |
| 3:1 | 1 | 3 |
| 1:1 | 0 | 3 |
| 0.3:1 | −1 | −2 |

| | ICP 27 (5 µg) + MPL (25 µg) + QS21 (10 µg) + SB26 | |
|---|---|---|
| E:T | P815 | P815 transfectés avec ICP27 clone 121 |
| 100:1 | 2 | 20 |
| 30:1 | 0 | 17 |
| 10:1 | 3 | 19 |
| 3:1 | 3 | 8 |
| 1:1 | 1 | 6 |
| 0.3:1 | 2 | 3 |

Low ICP27 specific % lysis was obtained in immunization groups:

ICP 27 (5 µg)+QS21 (10 µg)

ICP 27 (5 µg)+SB26

ICP 27 (5 µg)+MPL (25 µg)+QS21 (10 µg)

ICP 27 (5 µg)+MPL (25 µg)+QS21 (10 µg)+SB26 while

ICP 27 (5 µg)

ICP 27 (5 µg)+MPL (25 µg) were negative.

Thus these data show induction of CTL by recombinant NS1-ICP27 in oil-in-water emulsion alone or with QS21 and MPL; or with QS21.

b) Groups of 5 Balb/c mice were vaccinated in the footpad with the different vaccines (NS1-1CP27/NS1-ICP27 MPL+QS21/NS1-ICP27 SB26=MPL and QS21/adjuvant alone). One dose contained 10 µg NS1-ICP27, 10 µg MPL and 10 µg QS21.

Two vaccinations were given at days 0 and 7. Mice were challenged at day 14 with 5.2 $10^3$ TCID50 of HSV2 strain MS. The appearance of zosteriform lesions and deaths were recorded until day 14 post challenge.

ICP27 of HSV2 was expressed in *E. coli* as a fusion protein with NS1 fragment of influenza virus. The protective efficacy of the purified recombinant protein was evaluated in the murine zosteriform model, in combination with MPL QS21 formulations. Balb/c mice given two vaccinations with NS1-ICP27 combined either with MPL+QS21 or with an oil in water emulsion (SB26)+MPL and QS21 were completely protected against disease (no zosteriform lesions) and death following HSV2 wild type challenge. In contrast, protection was not observed in the mice vaccinated either with NS1-ICP27 alone or with NS1-ICP27 combined with SB26 without MPL and QS21.

TABLE 1

Vehicles two fold concentrated

| Emulsions SB | Tocopherol % | Squalene % | Tween 80% | Span 85% | Lecithin % | Size |
|---|---|---|---|---|---|---|
| 26 | 5 | 5 | 0.4 | 0 | 0 | 500 nm 90–100% 800 nm 10–0% |
| 26.1 | 5 | 5 | 0.4 | 0 | 0.1 | 500 nm |
| 63 | 5 | 5 | 0.6 | 0 | 0 | 500 nm |
| 64 | 5 | 5 | 0.8 | 0 | 0 | 500 nm |
| 61 | 5 | 5 | 1 | 0 | 0 | 250–300 nm |
| 62 | 5 | 5 | 2 | 0 | 0 | 180 nm |
| 40 | 5 | 5 | 0.4 | 1 | 0 | 500 nm 80–100% 800 nm 20–0% |
| 40.1 | 5 | 5 | 0.4 | 1 | 0.1 | 500 nm |
| 60 | 5 | 5 | 1 | 1 | 0 | 300 nm |
| 65 | 5 | 5 | 0.4 | 1.5 | 0 | 500 nm |
| 66 | 5 | 5 | 0.4 | 2 | 0 | 500 nm |

TABLE 2

HIV gp 120W61D/MOUSE IMMUNOGENICITY (94243)/BALB/C(F.P.)

| GROUPS | IMMUNOGEN (dose)/FORMULATION | ELISA TITERS (7 days PII) | %IgG1 | %IgG2a | %IgG2b |
|---|---|---|---|---|---|
| 1 | gP120 10 μg | 494 | 100 | 0 | 0 |
| 2 | gP120 10 μg + 3D-MPL 5 μg | 4164 | 54 | 15 | 32 |
| 3 | gP120 10 μg + QS21 5 μg | 21515 | 89 | 4 | 8 |
| 4 | gP120 10 μg + 3D-MPL + QS21 | 52749 | 22 | 60 | 18 |
| 5 | gP120 10 μg/SB26 | 12205 | 94 | 2 | 4 |
| 6 | gP120 10 μg/SB26 + 3D-MPL | 87388 | 31 | 42 | 27 |
| 7 | gP120 10 μg/SB26 + QS21 | 51020 | 73 | 15 | 13 |
| 8 | gP120 10 μg/SB26 + 3D-MPL + QS21 | 178169 | 23 | 57 | 21 |
| 9 | SB26 + 3D-MPL + QS21/gP120 10 μg | 185704 | 22 | 60 | 19 |
| 11 | gP120 10 μg/SB62 | 10348 | 92 | 8 | 0 |
| 12 | gP120 10 μg/SB62 + 3D-MPL + QS21 | 21739 | 54 | 37 | 9 |
| 13 | gP120 10 μg/SB40 | 36320 | 90 | 7 | 4 |
| 14 | gP120 10 μg/SB40 + 3D-MPL | 285219 | 31 | 44 | 25 |
| 15 | gP120 10 μg/SB40 + QS21 | 48953 | 78 | 15 | 7 |
| 16 | gP120 10 μg/SB40 + 3D-MPL + QS21 | 209217 | 14 | 67 | 18 |
| 17 | gP120 10 μg/SB61 | <50 | — | — | — |
| 18 | gP120 10 μg/SB61 + 3D-MPL | 77515 | 31 | 50 | 19 |
| 19 | gP120 10 μg/SB61 + QS21 | 40737 | 74 | 13 | 13 |
| 20 | gP120 10 μg/SB61 + 3D-MPL + QS21 | 59673 | 29 | 57 | 14 |
| 21 | gP120 5 μg/SB26 | 25089 | 99 | 0 | 1 |
| 22 | gP120 5 μg/SB26 + 3D-MPL + QS21 | 242736 | 18 | 61 | 21 |

ELISA titers to gp 120 W61D: geomean of 5 individual titers, calculated by LINEST

TABLE 3

3D-MPL based formulations: HIV project Monkey studies

| Read-Out | GMT ELisa W61 D | | GMT Neut. MN | | DTH in vivo | CMI in vitro | | |
|---|---|---|---|---|---|---|---|---|
| Formulation | P11 | P111 | P11 | P111 | | LP | IL-2 | γIFN |
| gp120(100 μg)/o/w + MPL + QS21 | 60523 | 93410 | 1:500 | >1:3200 | + | + | ND | + |
| gp120(20 μg)/o/w + MPL + QS21 | 52026 | 50150 | 1:500 | 1:2400 | + | + | ND | + |
| "Historical" gp120(100 μg)/o/w + MPL in guinea pigs | | 20064 | | | | | | |

What is claimed is:

1. A vaccine composition comprising an antigen and/or antigenic composition, QS21, 3-De-O-acylated monophosphoryl lipid A (3D-MPL) and an oil in water emulsion wherein the oil in water emulsion comprises a metabolizable oil, alpha tocopherol and TWEEN 80 (polyoxyethelene sorbitan monooleate).

2. The vaccine composition according to claim 1 wherein said metabolizable oil is squalene.

3. The vaccine composition according to claim 2 wherein the ratio of QS21:3D-MPL is from 1:10 to 10:1.

4. The vaccine composition according to claim 3 wherein said ratio is from 1:1 to 1:2.5.

5. The vaccine composition according to claim 1 wherein said vaccine is capable of invoking a cytolytic T cell response to said antigen and/or antigenic composition in a mammal.

6. The vaccine composition according to claim 1 wherein said vaccine is capable of stimulating interferon γ production.

7. An immunogenic composition comprising an antigen and/or antigenic composition, QS21, 3-De-O-acylated monophosphoryl lipid A (3D-MPL) and an oil in water emulsion wherein the oil in water emulsion comprises a metabolizable oil, alpha tocopherol and TWEEN 80 (polyoxyethelene sorbitan monooleate) wherein said antigen and/or antigenic composition is selected from the group consisting of Herpes Simplex Virus type 1, Herpes Simplex Virus type 2, Human cytomegalovirus, Hepatitis A, Hepatitis B, Hepatitis C, Hepatitis E, Respiratory Syncytial Virus, Human papilloma Virus, Influenza Virus, Salmonella, Neisseria, Borrelia, Chlamydia, Bordetella, Plasmodium and Toxoplasma.

8. An immunogenic composition comprising an antigen and/or antigenic composition, QS21, 3-De-O-acylated monophosphoryl lipid A (3D-MPL) and an oil in water emulsion wherein the oil in water emulsion comprises a metabolizable oil, alpha tocopherol and TWEEN 80 (polyoxyethelene sorbitan monooleate) wherein the antigen and/or antigenic composition is a tumor antigen.

9. A method of treating a mammal having a viral, bacterial or parasitic infection by administering a therapeutically safe and effective amount of the immunogenic composition of claim 7.

10. A method of treating a mammal susceptible to a viral, bacterial or parasitic infection by administering a prophylactically safe and effective amount of the immunogenic composition of claim 7.

11. A method of treating a mammal having cancer by administering a therapeutically safe and effective amount of the immunogenic composition of claim 8.

12. A process for making a vaccine according to claim 1 comprising admixing QS21, 3D-MPL and the oil and water emulsion with an antigen or antigen composition.

13. An immunogenic composition comprising an antigen and/or antigenic composition, QS21, 3-De-O-acylated monophosphoryl lipid A (3D-MPL) and an oil in water emulsion wherein the oil in water emulsion comprises a metabolizable oil, alpha tocopherol and TWEEN 80 (polyoxyethelene sorbitan monooleate) wherein said antigen and/or antigenic composition is selected from the group consisting of Human Immunodeficiency Virus and Feline Immunodeficiency Virus.

14. A method of treating a mammal having a viral infection by administering a therapeutically safe and effective amount of the immunogenic composition of claim 13.

15. A method of treating a mammal susceptible to a viral infection by administering a prophylactically safe and effective amount of the immunogenic composition of claim 13.

* * * * *